US009612185B2

(12) United States Patent
Superfine et al.

(10) Patent No.: US 9,612,185 B2
(45) Date of Patent: Apr. 4, 2017

(54) METHODS AND SYSTEMS FOR USING ACTUATED SURFACE-ATTACHED POSTS FOR ASSESSING BIOFLUID RHEOLOGY

(71) Applicant: The University of North Carolina at Chapel Hill, Chapel Hill, NC (US)

(72) Inventors: Richard Superfine, Chapel Hill, NC (US); Richard Chasen Spero, Chapel Hill, NC (US); Adam Richard Shields, Springfield, VA (US); Benjamin Aaron Evans, Chapel Hill, NC (US); Briana Lee Fiser, High Point, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/997,111

(22) Filed: Jan. 15, 2016

(65) Prior Publication Data
US 2016/0209313 A1   Jul. 21, 2016

Related U.S. Application Data

(62) Division of application No. 14/016,007, filed on Aug. 30, 2013, now Pat. No. 9,238,869, which is a division
(Continued)

(51) Int. Cl.
*C25F 3/00*      (2006.01)
*G01N 11/16*     (2006.01)
(Continued)

(52) U.S. Cl.
CPC ............ *G01N 11/16* (2013.01); *B01L 3/5085* (2013.01); *B29C 39/026* (2013.01); *C23F 1/04* (2013.01);
(Continued)

(58) Field of Classification Search
CPC .................... C23F 1/04; B82Y 10/00
(Continued)

(56) References Cited

U.S. PATENT DOCUMENTS 4,408,277 A   10/1983   Cortellini et al.
4,462,096 A    7/1984   Kusaka
(Continued)

FOREIGN PATENT DOCUMENTS

JP           5511949       4/2014
WO   WO 02/093738 A2   11/2002
(Continued)

OTHER PUBLICATIONS

Sniadecki et al. "Magnetic microposts for mechanical stimiulation of biolgical cells: Fabrication, characterization, and analysis" Review of Scientific Instruments, Aip, Melville, Ny, US, vol. 79, No. 4, Apr. 16, 2008.*
(Continued)

*Primary Examiner* — Roberts Culbert
(74) *Attorney, Agent, or Firm* — Jenkins, Wilson, Taylor & Hunt, P.A.

(57) ABSTRACT

Methods, systems, and computer readable media for using actuated surface-attached posts for assessing biofluid rheology are disclosed. According to one aspect, a method for testing properties of a biofluid specimen includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method further includes measuring the motion of at least one of the microposts in response to the actuation force and determin-
(Continued)

ing a property of the specimen based on the measured motion of the at least one micropost.

4 Claims, 15 Drawing Sheets

Related U.S. Application Data of application No. 13/380,564, filed as application No. PCT/US2010/040011 on Jun. 25, 2010, now Pat. No. 8,586,368.

(60) Provisional application No. 61/220,563, filed on Jun. 25, 2009, provisional application No. 61/234,177, filed on Aug. 14, 2009.

(51) Int. Cl.
| | | |
|---|---|---|
| G01N 33/49 | (2006.01) | |
| C23F 1/04 | (2006.01) | |
| B01L 3/00 | (2006.01) | |
| G01N 29/02 | (2006.01) | |
| B29C 39/02 | (2006.01) | |
| B82Y 15/00 | (2011.01) | |
| B29K 83/00 | (2006.01) | |
| B29L 31/00 | (2006.01) | |

(52) U.S. Cl.
CPC ....... *G01N 29/022* (2013.01); *G01N 33/4905* (2013.01); *B01L 2300/0636* (2013.01); *B01L 2300/0663* (2013.01); *B01L 2300/0851* (2013.01); *B29K 2083/00* (2013.01); *B29K 2869/00* (2013.01); *B29L 2031/756* (2013.01); *B82Y 15/00* (2013.01); *G01N 2291/0255* (2013.01); *G01N 2291/0256* (2013.01); *G01N 2291/02827* (2013.01)

(58) Field of Classification Search
USPC .................................................... 216/11, 22
See application file for complete search history.

(56) References Cited

U.S. PATENT DOCUMENTS

| | | |
|---|---|---|
| 5,110,727 A | 5/1992 | Oberhardt |
| 5,206,504 A | 4/1993 | Sridharan |
| 5,350,676 A | 9/1994 | Oberhardt et al. |
| 5,436,448 A | 7/1995 | Hosaka et al. |
| 5,458,785 A | 10/1995 | Howe et al. |
| 5,638,303 A | 6/1997 | Edberg et al. |
| 5,698,843 A | 12/1997 | Phak |
| 5,777,215 A | 7/1998 | Calatzis et al. |
| 5,976,369 A | 11/1999 | Howe et al. |
| 6,067,207 A | 5/2000 | Kurita |
| 6,162,364 A | 12/2000 | Tillotson et al. |
| 6,269,324 B1 | 7/2001 | Rakijas et al. |
| 6,330,824 B1 | 12/2001 | Erie et al. |
| 6,370,107 B1 | 4/2002 | Hosaka et al. |
| 6,442,416 B1 | 8/2002 | Schultz |
| 6,470,226 B1 | 10/2002 | Olesen et al. |
| 6,496,332 B1 | 12/2002 | Okazaki et al. |
| 6,503,195 B1 | 1/2003 | Keller et al. |
| 6,545,580 B2 | 4/2003 | Hegde et al. |
| 6,549,004 B1 | 4/2003 | Prigge |
| 6,596,076 B1 | 7/2003 | Wakayama |
| 6,624,919 B2 | 9/2003 | Lambert |
| 6,650,213 B1 | 11/2003 | Sakurai et al. |
| 6,716,642 B1 | 4/2004 | Wu et al. |
| 6,794,197 B1 | 9/2004 | Indermuhle et al. |
| 6,881,954 B1 | 4/2005 | Mormoto et al. |
| 6,885,266 B2 | 4/2005 | Ochi-Okorie |
| 6,936,471 B2 | 8/2005 | Hajduk et al. |
| 7,119,645 B2 | 10/2006 | Vicci et al. |
| 7,189,969 B2 | 3/2007 | Vicci et al. |
| 7,191,092 B2 | 3/2007 | Vicci et al. |
| 7,305,319 B2 | 12/2007 | Vicci et al. |
| 8,490,469 B2 | 7/2013 | Superfine et al. |
| 8,586,368 B2 | 11/2013 | Superfine et al. |
| 9,238,869 B2 | 1/2016 | Superfine et al. |
| 2001/0055462 A1 | 12/2001 | Seibel |
| 2003/0118222 A1 | 6/2003 | Foran et al. |
| 2003/0203271 A1 | 10/2003 | Morse et al. |
| 2004/0191915 A1 | 9/2004 | Bawendi et al. |
| 2004/0241759 A1 | 12/2004 | Tozer et al. |
| 2004/0244470 A1 | 12/2004 | Vicci et al. |
| 2004/0262210 A1 | 12/2004 | Westervelt et al. |
| 2005/0015001 A1 | 1/2005 | Lec et al. |
| 2005/0064395 A1 | 3/2005 | Israel et al. |
| 2005/0276727 A1 | 12/2005 | Pawliszyn et al. |
| 2006/0068107 A1 | 3/2006 | Madou et al. |
| 2006/0219904 A1 | 10/2006 | Vicci et al. |
| 2006/0229842 A1 | 10/2006 | Vicci et al. |
| 2007/0031819 A1 | 2/2007 | Koschwanez et al. |
| 2008/0261261 A1 | 10/2008 | Grimes et al. |
| 2009/0220561 A1 | 9/2009 | Jin et al. |
| 2011/0240476 A1 | 10/2011 | Wang et al. |
| 2012/0107851 A1 | 5/2012 | Killard et al. |
| 2012/0156791 A1 | 6/2012 | Superfine et al. |

FOREIGN PATENT DOCUMENTS

| | | |
|---|---|---|
| WO | WO 03/029921 | 4/2003 |
| WO | WO 2008/139401 A2 | 11/2008 |

OTHER PUBLICATIONS

Notice of Allowance and Fee(s) Due for U.S. Appl. No. 14/016,007 (Sep. 14, 2015).

Applicant-Interview Summary for U.S. Appl. No. 14/016,007 (Aug. 19, 2015).

Non-Final Office Action for U.S. Appl. No. 14/016,007 (May 18, 2015).

Extended European Search Report for European Application No. 10792732.9 (Mar. 3, 2015).

Notice of Allowance and Fee(s) Due for U.S. Appl. No. 13/380,564 (Jul. 12, 2013).

Restriction and/or Election Requirement for U.S. Appl. No. 13/380,564 (May 24, 2013).

Supplemental Notice of Allowability for U.S. Appl. No. 12/528,312 (Apr. 25, 2013).

Notice of Allowance and Fee(s) Due for U.S. Appl. No. 12/528,312 (Mar. 21, 2013).

Non-Final Official Action for U.S. Appl. No. 12/528,312 (Jun. 19, 2012).

Communication of European publication number and information on the application of Article 67(3) EPC for European Application No. 10792732.9 (Apr. 4, 2012).

Notification of Transmittal of the International Search Report and the Written Opinion of the International Searching Authority, or the Declaration for International Application No. PCT/US2010/040011 (Feb. 15, 2011).

Notification of Transmittal of the International Search Report and the Written Opinion of the International Searching Authority, or the Declaration for International Application No. PCT/US08/02331 (Jun. 25, 2008).

Belmiloud et al., "Rheological Behavior Probed by Vibrating Microcantilevers," Applied Physicis Letters, vol. 92, pp. 041907-041907-3 (Jan. 30, 2008).

Sniadecki et al., "Magnetic Microposts as an Approach to Apply Forces to Living Cells," Proceedings of Natual Academy of Sciences, vol. 104, No. 37 (Sep. 11, 2007).

Notice of Allowance and Fee(s) Due for U.S. Appl. No. 10/487,860 (Jul. 25, 2007).

Non-Final Office Action for U.S. Appl. No. 10/487,860 (Feb. 28, 2007).

Supplemental Notice of Allowability for U.S. Appl. No. 11/440,912 (Feb. 7, 2007).

(56) References Cited

OTHER PUBLICATIONS

Supplemental Notice of Allowability for U.S. Appl. No. 11/440,881 (Feb. 7, 2007).
Interview Summary for U.S. Appl. No. 10/487,860 (Jan. 22, 2007).
Yun et al., "Carbon Nanotube Array Smart Materials," SPIE, vol. 6172, pp. 617205-1-617205-12 (Dec. 31, 2006).
Supplemental Notice of Allowability for U.S. Appl. No. 10/786,427 (Aug. 17, 2006).
Notice of Allowance and Fee(s) Due for U.S. Appl. No. 11/440,912 (Jul. 25, 2006).
Notice of Allowance and Fee(s) Due for U.S. Appl. No. 11/440,881 (Jul. 25, 2006).
Final Official Action for U.S. Appl. No. 10/487,860 (Jul. 19, 2006).
Notice of Allowance and Fee(s) Due for U.S. Appl. No. 10/786,427 (Mar. 28, 2006).
3rdTech, "HiBall™-3100 Wide-Area Tracker and 3D Digitizer," 3rd Tech, Inc. (2006).
Non-Final Office Action in U.S. Appl. No. 10/487,860 (Dec. 7, 2005).
Restriction Requirement for U.S. Appl. No. 10/786,427 (Oct. 4, 2005).
Notification of Transmittal of International Preliminary Examination Report for International Application No. PCT/US02/30853 (Mar. 4, 2004).
Notification of Transmittal of the International Search Report or the Declaration for International Application No. PCT/US02/30853 (May 7, 2003).
Prisco et al., "Point-of-Care Testing of Hemostasis in Cardiac Surgery," Thrombosis Journal, vol. 1, No. 1, 10 pgs. (May 2003).
Jian Ling, "Toward Raman Spectroscopy of Biological Tissue for Cancer Diagnosis", Southwest Research Institute IR&D, 10-9359 (Feb. 2003).
Wilde, "Three-Dimensional Force Microscope," (Downloaded from the Internet on Jun. 24, 2002).
"MFP-3D™ Atomic Force Microscope Power and Flexibility in One Complete System" Asylum Research, pp. 1-4 (Jun. 5, 2002).
Lee et al., "Microelectromagnets for the Control of Magnetic Nanoparticles," Applied Physics Letters, vol. 79, No. 20, pp. 3308-3310 (Nov. 12, 2001).
Vicci, "A 3D Magnetic Force Manipulator DC Prototype," Department of Computer Science, UNC Chapel Hill (Oct. 17, 2001).
Requicha et al., "Manipulation of Nanoscale Components with the AFM: Principles and Applications," Proceedings of the 2001 1st IEEE Conference on Nanotechnology, pp. 81-86 (Oct. 2001).
Baldis, "Institute for Laser Science and Applications," U.S. Department of Energy, UCRL-ID-145269, pp. 53-55 (Aug. 27, 2001).
Vicci, "A 3D Magnetic Force Manipulator DC Prototype," Department of Computer Science, UNC Chapel Hill (Jul. 3, 2001).
Heaton et al., "Scanning Probe/Atomic Force Microscopy: Technology Overview and Update," pp. 1-8 (Mar. 2001).
Welch et al., "High-Performance Wide-Area Optical Tracking—The HiBall Tracking System," Presence, vol. 10, No. 1, Massachusetts Institute of Technology (Feb. 2001).
Choi et al., "An On-Chip Magnetic Bead Separator Using Spiral Electromagnets with Semi-Encapsulated Permalloy," Biosensors & Bioelectronics 16, pp. 409-416 (2001).
"Atomic Force Microscopy," Veeco Metrology Group (Downloaded from the Internet on Jun. 24, 2002) (Copyright 2001).
Keller et al., "Real-time Structured Light Depth Extraction," Three Dimensional Image Capture and Applications III; SPIE Proceedings, p. 11-18; Photonics West—Electronic Imaging 2000 (Jan. 2000).
Choi et al., "A New Magnetic Bead-Based, Filterless Bio-Separator with Planar Electromagnet Surfaces for Integrated Bio-Detection Systems," Sensors and Actuators B 68, pp. 34-39 (2000).
Stavros Demos, "Endoscopic Subsurface Optical Imaging for Cancer Detection," Institute for Laser Science and Applications Report 2000 (2000).
Welch et al., "The HiBall Tracker: High-Performance Wide-Area Tracking for Virtual and Augmented Environments," Symposium on Virtual Reality Software and Technology, University College London (Dec. 20-22, 1999).
Ahn et al., "Micromachined Planar Inductors on Silicon Wafer for MEMS Applications," IEEE Transactions on Industrial Electronics, vol. 45, No. 6, pp. 866-876 (Dec. 1998).
Drndić et al., "Micro-Electromagnets for Atom Manipulation," Applied Physics Letters, vol. 72, No. 22, pp. 2906-2908 (Jun. 1, 1998).
Ahn et al., "A Fully Integrated Micromachined Magnetic Particle Separator," Journal of Microelectromechanical Systems, vol. 5, No. 3, pp. 151-158 (Sep. 1996).
Hosaka et al., "Damping Characteristics of Beam-Shaped Micro-Oscillators," Elsevier Science Sensors and Actuators, vol. 49, pp. 87-95 (Feb. 1995).
Ahn et al., "A Fully Integrated Planar Toroidal Inductor with a Micromachined Nickel-Iron Magnetic Bar," IEEE Transactions on Components, Packaging, and Manufacturing Technology—Part A, vol. 17, No. 3, pp. 463-469 (Sep. 1994).
"The First Commercial Low Temperature Near-field Optical Microscope," NSOM/AFM 100 Confocal LT™, pp. 1-2 (Publication Date Unknown).

\* cited by examiner

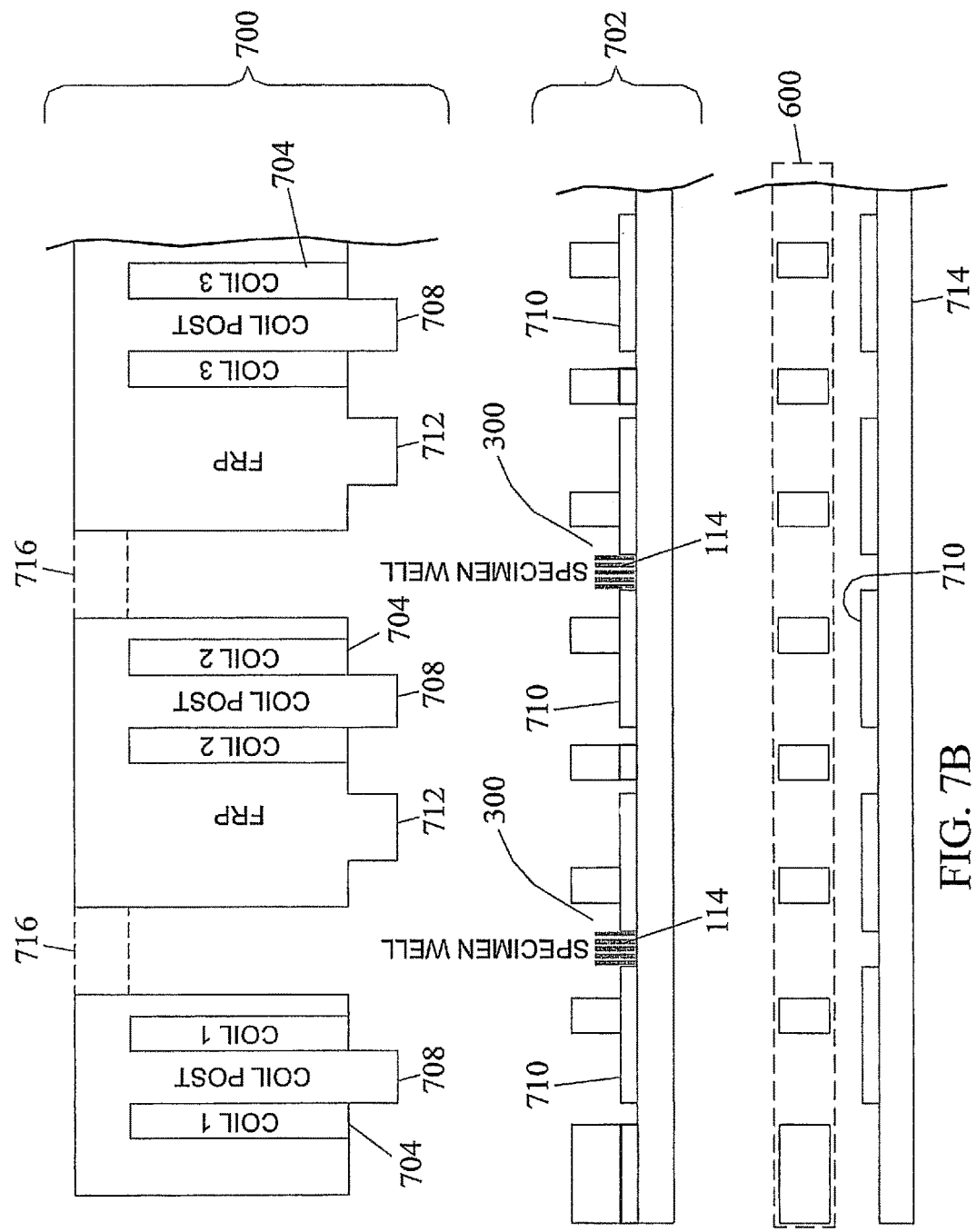

METHODS AND SYSTEMS FOR USING ACTUATED SURFACE-ATTACHED POSTS FOR ASSESSING BIOFLUID RHEOLOGY

PRIORITY CLAIM

This application is a divisional of U.S. patent application Ser. No. 14/016,007, filed Aug. 30, 2013, which is a divisional of U.S. patent application Ser. No. 13/380,564 (now U.S. Pat. No. 8,586,368), filed Mar. 2, 2012, which is a national stage application under 35 U.S.C. § 371 of PCT Patent Application No. PCT/US2010/040011 filed Jun. 25, 2010, which claims the benefit of U.S. Provisional Patent Application Ser. No. 61/220,563, filed Jun. 25, 2009; and which claims the benefit of U.S. Provisional Patent Application Ser. No. 61/234,177, filed Aug. 14, 2009; the disclosure of each of which is incorporated herein by reference in its entirety.

GOVERNMENT INTEREST

This invention was made with government support under Grant No. CMS-0507151 awarded by the National Science Foundation and Grant No. EB002025 awarded by the National Institutes of Health. The government has certain rights in the invention.

TECHNICAL FIELD

The subject matter described herein relates to methods and systems for measuring physical properties of biofluids using surface-attached actuated microposts. More particularly, the subject matter described herein relates to methods and systems for using surface-attached actuated microposts for assessing biofluid rheology.

BACKGROUND

The viscoelasticity of biofluids, such as blood clots or mucus, is critical to their performance. Measurement of viscoelastic properties of these fluids can provide valuable information to medical professionals to aid in the diagnosis and treatment of patients. For example, the speed and strength at which a blood clot forms may be affected by genetics, illness, medication, or environment. Analyzing the physical properties of a blood clot may provide important information that is useful in determining how well a treatment is working or is likely to work, or perhaps that a treatment intervention is necessary.

Currently, clot elasticity is measured either at the point of care (POC), usually accompanying surgery, or within an analytical lab setting. Techniques for understanding clot viscoelasticity in a point of care system use several different strategies. One technology employs flow through a tube that is monitored in some way, such as by an optical detection. Another technology uses magnetic beads that become suspended in the developing clot, and the beads are caused to move through the application of a magnetic field. The detection of the moving beads is performed by optics, and the cessation of the bead movement is an indication that the clot has formed.

In an analytical lab setting, techniques such as thromboelastography (TEG) can test the efficiency of coagulation in the blood. TEG uses a macroscopic quantity of specimen and measures the viscoelasticity by moving two surfaces with respect to each other in shear. The geometry is usually that of concentric cylinders. Similar techniques are used for measuring the viscoelasticity of other biofluids such as mucus.

There are disadvantages associated with the current methods of testing rheological properties of biofluids. Laboratory techniques such as TEG are not implemented as high-throughput instruments, so tests must be performed essentially one at a time. Point of care technologies are not as sensitive or quantitative as laboratory tests and so cannot replace laboratory analysis. In addition, macroscopic quantities of specimens are generally needed for laboratory analysis.

Accordingly, in light of these disadvantages associated with biofluid rheology techniques, there exists a need for methods and systems for using surface-attached actuated microposts for assessing biofluid rheology.

SUMMARY

According to one aspect, the subject matter described herein includes a method that includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method further includes measuring the motion of at least one of the microposts in response to the actuation force and determining a property of the specimen based on the measured motion of the at least one micropost.

According to another aspect, the subject matter described herein includes a system for measuring a property of a biofluid specimen which includes a micropost array having a plurality of microposts extending outwards from a substrate, an actuation unit for generating an actuation force in proximity to the micropost to compel at least some of the microposts to exhibit motion, a motion detection unit for measuring the motion of at least one of the microposts exhibiting motion, and a processing unit for determining a property of the specimen based on the measured motion of the microposts.

According to another aspect, the subject matter described herein includes a method of fabricating a micropost array that includes depositing, into at least some pores of a substrate, a material which has at least one of a metallic, magnetic, thermal, optical, and ferroelectric characteristic. The method further includes filling the pores with a curable material that is flexible when cured, such that the curable material interconnects the pores along at least one planar surface of the substrate. The method further includes curing the material and removing the substrate to form the micropost array.

According to another aspect, the subject matter described herein includes a method of fabricating a micropost array that includes filling a plurality of vertically-aligned pores in a substrate with a curable material that is flexible when cured. The curable material includes a plurality of nanoparticles. The method further includes applying a force to draw the nanoparticles in one direction within the pores such that the distribution of nanoparticles is non-uniform. The method further includes curing the curable material and removing the substrate to form the micropost array.

The subject matter described herein for using surface-attached actuated microposts for assessing biofluid rheology may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which:

FIG. 7B is a diagram illustrating a cross-section view of a multiforce high-throughput screening system according to an embodiment of the subject matter described herein;

DETAILED DESCRIPTION

Figure 1A:
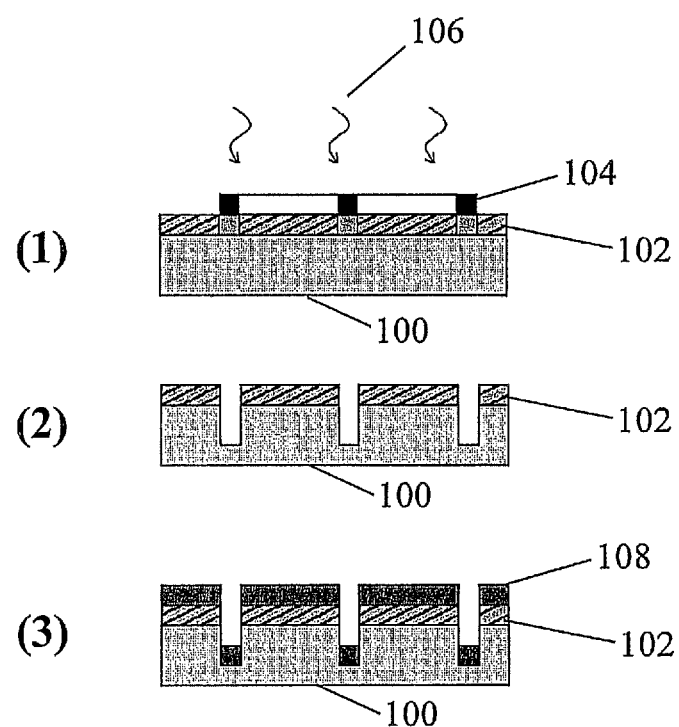
FIGS. 1A and 1B are diagrams illustrating an exemplary method for fabricating a micropost array according to an embodiment of the subject matter described herein.

In accordance with the subject matter disclosed herein, systems, methods, and computer readable media are provided for methods and systems for using actuated surface-attached posts to assess biofluid rheology. The subject matter disclosed herein is directed to the application of an applied force, such as an electric, magnetic, thermal, or sonic force, to flexible microposts of a micropost array, where the array is made up at least in part of an elastic material, such as an elastomer. The viscoelastic properties of a biofluid specimen may be measured by placing the biofluid on or near such microposts, and applying an actuating force to the microposts. The subject matter further includes measuring the movement, or change in movement over time, of the microposts. Microposts of a micropost array may be located, for example, in a multiwell plate for high-throughput applications, on a tab to be used with a point of care device, or in a format appropriate for a bench-top laboratory device.

There are many possible embodiments that fall within the scope of the present subject matter. The broader inventive concept will now be discussed, as a basis for detailed embodiments to follow. Embodiments of the present subject matter are based on the detection and measurement of movement exhibited by microposts in a micropost array on which a specimen of interest is placed and an actuation force is applied. The detected movement may then be analyzed to obtain the desired information about the specimen.

For example, one exemplary method of the present subject matter includes placing a biofluid specimen, such as blood, onto a micropost array having a plurality of flexible microposts extending outwards from a substrate base.

The term "micropost array" is herein used to describe an array of small, posts, extending outwards from a substrate, that typically range from 1 to 100 micrometers in height. In one embodiment, microposts of a micropost array may be vertically-aligned. Notably, each micropost includes a proximal end that is attached to the substrate base and a distal end or tip that is opposite the proximal end. The term "biofluid" is used herein to refer to any fluid created by the body, including but not limited to blood, mucus (e.g. sputum, ocular fluid, sinus fluid, and cervical fluid), synovial fluid, pus, and excretions resulting from burns.

Once the biofluid specimen is in place, an actuation force is generated in proximity to the micropost array that compels at least some of the microposts to exhibit motion. As used herein, the term "actuation force" refers to the force applied to the microposts. For example, the actuation force may include a magnetic, thermal, sonic, or electric force. Notably, the actuation force may be applied as a function of frequency or amplitude, or as an impulse force (i.e., a step function). Similarly, other actuation forces may be used without departing from the scope of the present subject matter, such as fluid flow across the micropost array.

As the microposts exhibit motion in response to the actuation force, the motion of the microposts may be measured or detected. The motion detection system may be configured to measure the motion of individual or specific microposts, groups of microposts, or all the microposts. The means for detecting and measuring this micropost behavior may include an optical, magnetic, sonic, or electrical tracking system. These detection systems are described in greater detail below.

Lastly, after the motion of the microposts has been measured, the measurement data is provided to a processing unit that processes the data in order to determine at least one property of the specimen based on the measured motion. For example, as a blood specimen begins to clot, the motion of the microposts becomes restricted, and the resulting measurements may be used to determine clotting time.

Exemplary properties of a biofluid specimen may include clotting characteristics, chemical properties, rheological properties, physical properties, and the like. In one embodiment, the processing unit may be configured to use existing clot measurement assays, including, but not limited to, PT, PTT, APPT, and INR assays, to determine clotting characteristics of a biofluid specimen (i.e., blood). The processing unit may also or alternatively be configured to determine the clotting time of blood, as described above, or the breakdown time of a blood clot (i.e. measurements over a period of time). In another embodiment, particularly where the motion of a particular micropost or group of microposts was measured, the processing unit may be configured to use the micropost motion measurement data to determine the heterogeneity of the specimen. Other embodiments may determine, for example, the effect of a drug on a specimen or may detect the presence of DNA in a sample. Notably, data of this type has many practical uses, such as for detecting diseases or prescribing medication based on the rheological properties of the biofluid specimen. Similarly, the processing unit may be used as a chemical sensor by adding a reagent or enzyme to the microposts.

Materials used to fabricate the micropost array may vary. The micropost array includes at least some elastic material, e.g. an elastomer, to allow for the reactive motion of the microposts. The microposts themselves may be entirely or partially made up of an elastomer on either a flexible or non-flexible substrate material. Alternatively, the microposts may be made up of a non-flexible material, so long as the substrate base material is elastic, to allow the microposts to move in response to the specimen and the applied force. A micropost array as described herein may be considered biomimetic cilia, i.e. an array of silicone-formed structures that resembles biological cilia.

In one embodiment, the elastomer composing the micropost may include nanoparticles of various materials dispersed throughout, which allows for the fine-tuning of properties of the microposts for particular applications. As used herein, nanoparticles include, but are not limited to metallic, ferromagnetic, ferroelectric, thermal, or optical particles. Furthermore, nanoparticles suspended in the micropost material may be non-uniformly distributed throughout the microposts, such that a higher concentration of particles may exist on one side, or end, of the microposts. Alternatively, the microposts may be fabricated to include a piece of a solid material, such as a rod or a shell, which may extend for the full height of a micropost or only a portion of the height of a micropost. Additional embodiments may include the coating of the microposts after array fabrication, which may be applied obliquely to coat one side of the microposts, particularly for thermal actuation methods.

The term "ferromagnetic" is used herein to refer to any magnetic material, including but not limited to ferromagnetic, diamagnetic, paramagnetic, super-paramagnetic, ferrimagnetic and ferrofluid materials. Likewise, the term "ferroelastomer" is used herein to refer to an elastomer having any type of magnetic nanoparticles dispersed throughout, regardless of how the nanoparticles are bonded to the elastomer, and including but not limited to ferromagnetic, paramagnetic and super-paramagnetic particles. The term "ferroelectric" is used herein to refer to any dielectric material, including but not limited to piezoelectric, pyroelectric, and paraelectric materials.

The material selected for the micropost depends on the intended use of the micropost array, particularly with respect to the actuation method, i.e. the nature of the force to be applied to the microposts. When applying an electrical force, i.e. an electric actuation method, properties of the micropost material to consider include the dielectric constant, polarizability and charge of the material. For a magnetic actuation method, i.e. where a magnetic force is applied, significant properties of the micropost material include permeability and hysteresis.

Properties of the micropost material to consider for a thermal actuation method include the thermal expansion coefficient, absorbance and heat capacity of the material. When microposts are actuated by flow, i.e. a fluid is flowed across the microposts and the resultant post deflection is measured, factors to consider include the geometry (diameter and length) and elastic properties of the microposts.

Detection mechanisms for measuring movement of the microposts may also vary and typically depend on the fabrication material of the micropost array. Detection mechanisms may include, but are not limited to, magnetic, optical, sonic, or electric detection systems or devices. In one embodiment, a magnetic detection means would include magnetic material in the microposts, and may utilize pickup coils, microelectromechanical (MEM) systems, or solid state devices and systems. Similarly, in one embodiment, an optical detection means would include optical material in the microposts, i.e. materials or particles having optical properties including, but not limited to, absorptive, reflective, or scattering properties, in order to measure the reflection, transmission, or scattering of light as the microposts move, particularly when the microposts have been fabricated to include reflective material on their tips and/or lateral sides. In one embodiment, optical detection means may include an imaging system, a scattered-light measuring system, a reflected-light measuring system, or a transmitted-light measuring system. Sonic and electric detection methods may operate in similar manners. Detection and measurement of micropost movement may vary in coarseness. Namely, measurements may be performed on one or more individual microposts, a group of microposts, or all microposts associated with a particular specimen.

Regardless of the specific detection mechanism used in a given embodiment of the present subject matter, the detection mechanism is configured to measure the amplitude and phase of the micropost motion. In one embodiment, changes in amplitude or phase may be measured as a function of frequency. As the microposts oscillate in response to an applied actuation force, changes in amplitude or phase may be used to determine properties of the specimen being analyzed. A processing unit may be used to calculate, based on the measured motion of the microposts, a variety of properties of a biofluid specimen. For example, one such property may include clotting time, if the biofluid specimen is blood. The present subject matter may also be used for linear or non-linear rheology or for chemical sensing. When used for chemical sensing, a substance such as an enzyme, chemical, or drug may be applied to the microposts and/or the specimen surrounding the microposts, and the response of the specimen may be determined by measuring the motion of the microposts.

Reference will now be made in detail to exemplary embodiments of the present subject matter, examples of which are illustrated in the accompanying drawings. Wherever possible, the same reference numbers will be used throughout the drawings to refer to the same or like parts.

Figure 1B:
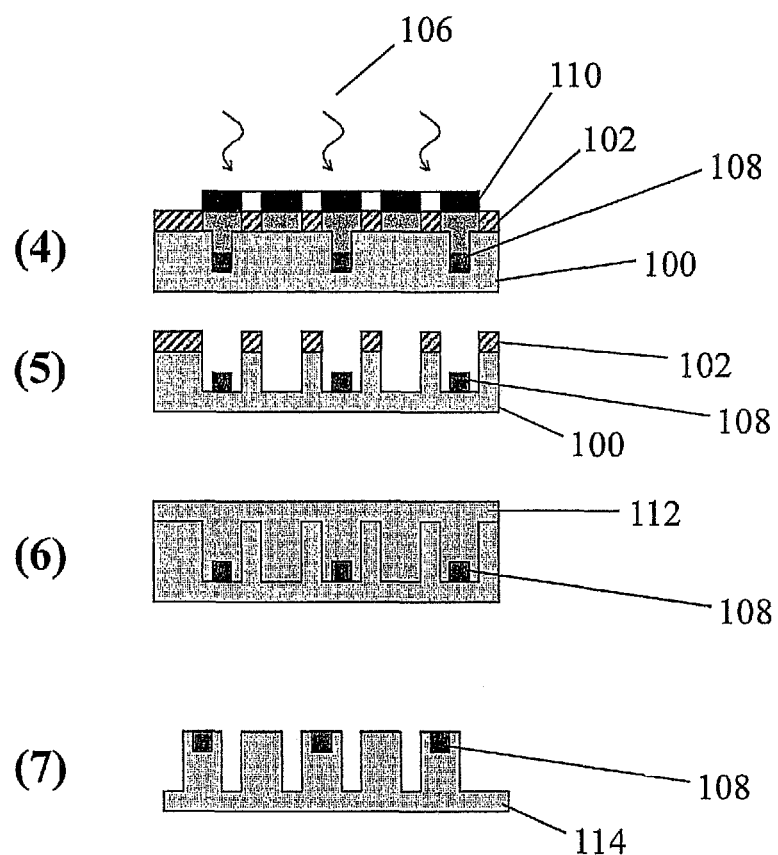

FIGS. 1A and 1B are diagrams illustrating an exemplary two-phase method for fabricating a micropost array according to an embodiment of the subject matter described herein. Phase 1 of an exemplary photolithographic fabrication method is illustrated in FIG. 1A. In step 1, silicon substrate 100 is coated with photoresist 102 and masked with mask 104, which may be a quartz mask with chrome features. Mask 104 defines the diameter and spacing for magnetic posts in the array. The masked photoresist is exposed to ultraviolet (UV) rays 106 and rinsed with commercial developer to remove the uncross-linked photoresist. In step 2, the uncovered areas of silicon substrate 100 are then etched. In one embodiment, the etching is conducted using a deep reactive ion etcher (DRIE) that creates a plurality of pores (as defined by the previously used mask) within the substrate. The depth of the etched pores defines the height of the microposts. In one embodiment, the depth of each of the etched pores is between six and twenty-five microns. In step 3, a ferromagnetic material (e.g., iron) is deposited onto the DRIE-etched silicon substrate 100. In one embodiment, iron layer 108 may be deposited using a plasma vapor deposition system or some other deposition technique. In one embodiment, iron layer 108 may be between one-third and one-half the height of the post, i.e. one-third to one-half of the depth of the etched pores. Subsequently, the remaining (cross-linked) photoresist 102 is removed, thereby also removing the undesired iron from the surface of substrate 100.

Phase 2 of the exemplary photolithographic fabrication method is illustrated in FIG. 1B. In step 4, silicon substrate 100, now etched to have a plurality of pores having iron deposited therein, is again coated with photoresist 102. Mask 110, which may also comprise a chrome mask, is then applied to photoresist-covered substrate 100 and photoresist layer 102 is exposed to UV rays 106. Uncross-linked photoresist is then removed using a commercial developer. Mask 110, which differs from mask 104, defines the diameter of the micropost material surrounding the deposited iron in magnetic microposts. Mask 110 also defines the diameter and spacing of non-magnetic microposts, i.e. mask 110 widens the pores around the deposited iron and creates new pores for microposts that will not be magnetic. In one embodiment, all microposts include deposited magnetic material. In another embodiment, some microposts of the micropost array do not include magnetic material. Using this exemplary method of fabrication, the location, arrangement, and number of microposts that will respond to an actuation force can be designed or controlled. In step 5, the exposed silicon from silicon substrate 102 is again etched (e.g., using DRIE) to the same depth as in phase 1. The remaining photoresist may be removed. In step 6, the newly created and widened pores are filled with uncured micropost material 112, such as polydimethylsiloxane (PDMS). The PDMS-filled silicon substrate 100 is then cured. In one embodiment, the substrate is cured at eighty degrees and for one hour. In step 7, the cured PDMS micropost array 114 is removed from silicon substrate 100. Micropost array 114 may be removed, for example, by gently peeling the cured PDMS off of silicon substrate 100 or by using a solution to specifically etch away the silicon, leaving behind only micropost array 114. For example, micropost array 114 is depicted in FIG. 1B as having a plurality of flexible, attached microposts, wherein at least some microposts contain a single piece of embedded iron essentially at the distal ends or tips.

In an alternate embodiment, a material such as a thin polycarbonate sheet may be used to mold the microposts rather than using a silicon substrate. Namely, only one photolithographic mask is used to define the size of the magnetic rod within each micropost. In this embodiment, all of the microposts of micropost array 114 include magnetic material. The fabrication process for this embodiment essentially follows the steps of phase 1 of the fabrication process illustrated in FIG. 1A. However, in this embodiment, prior to iron deposition, holes in the polycarbonate sheet may be backed with a material, such as silver, which may be deposited, for example, using a pulsed laser deposition system. The iron is then deposited and the remaining photoresist is removed in the same manner as described above. Phase 2 of this embodiment varies slightly from that described above in that additional pores are not created, i.e. there is no second mask, and the micropost array will only contain magnetic microposts rather than a combination of magnetic and non-magnetic microposts. The polycarbonate pores, each containing iron deposits, may then be widened by etching (e.g., using 4M sodium hydroxide). The widened pores are then filled with PDMS and cured as described above. After curing, the silver backing may be removed. In one embodiment, the silver backing is removed using a 50% nitric acid wash. The micropost array may then be removed from the polycarbonate sheet. For example, the array may be removed by using dichloromethane to dissolve the polycarbonate, which thereby releases the array.

Figure 1C:
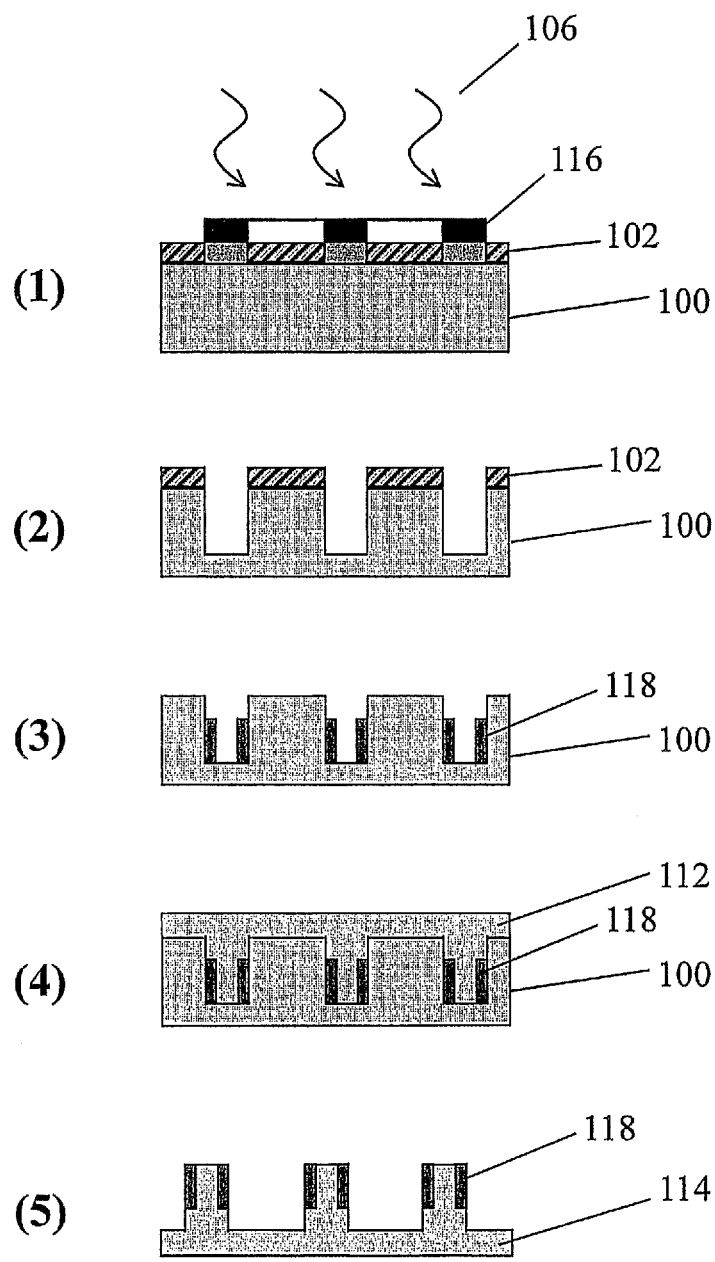
FIG. 1C is a diagram illustrating another exemplary fabrication method for fabricating a micropost array according to an embodiment of the subject matter described herein.

In an alternate embodiment, magnetic material may be deposited along the sidewalls of the pores to form a shell-like structure within the pore, using electrochemical deposition techniques. An exemplary fabrication process is illustrated in FIG. 1C. In step 1, silicon substrate 100 is coated with photoresist 102 and then masked with mask 116. In one embodiment, mask 116 is a quartz mask with chrome features. Mask 116 defines the diameter and spacing for all posts in the array. The masked photoresist is exposed to UV rays 106 and rinsed with commercial developer to remove the uncross-linked photoresist. In step 2, the uncovered areas of silicon substrate 100 are then etched, preferably with deep reactive ion etcher (DRIE), to create a plurality of pores within the substrate. The depth of the etched pores will determine the height of the microposts. In step 3, a magnetic material (e.g., nickel) is deposited into at least some of the DRIE-etched pores in silicon substrate 100 and the remaining (cross-linked) photoresist 102 is removed. Nickel layer 118 may be deposited using electrochemical deposition. Nickel layer 118 may line the sidewalls of the pores for the full height of the pores or may be selectively deposited only on, for example, the bottom half of the pore's sidewalls. Once the magnetic material has been deposited in the desired thickness and height, the pores are filled with curable micropost material 112 and cured in step 4. In step 5, the cured micropost array is removed from substrate 100, as described above in the description of FIG. 1B.

Figure 2:
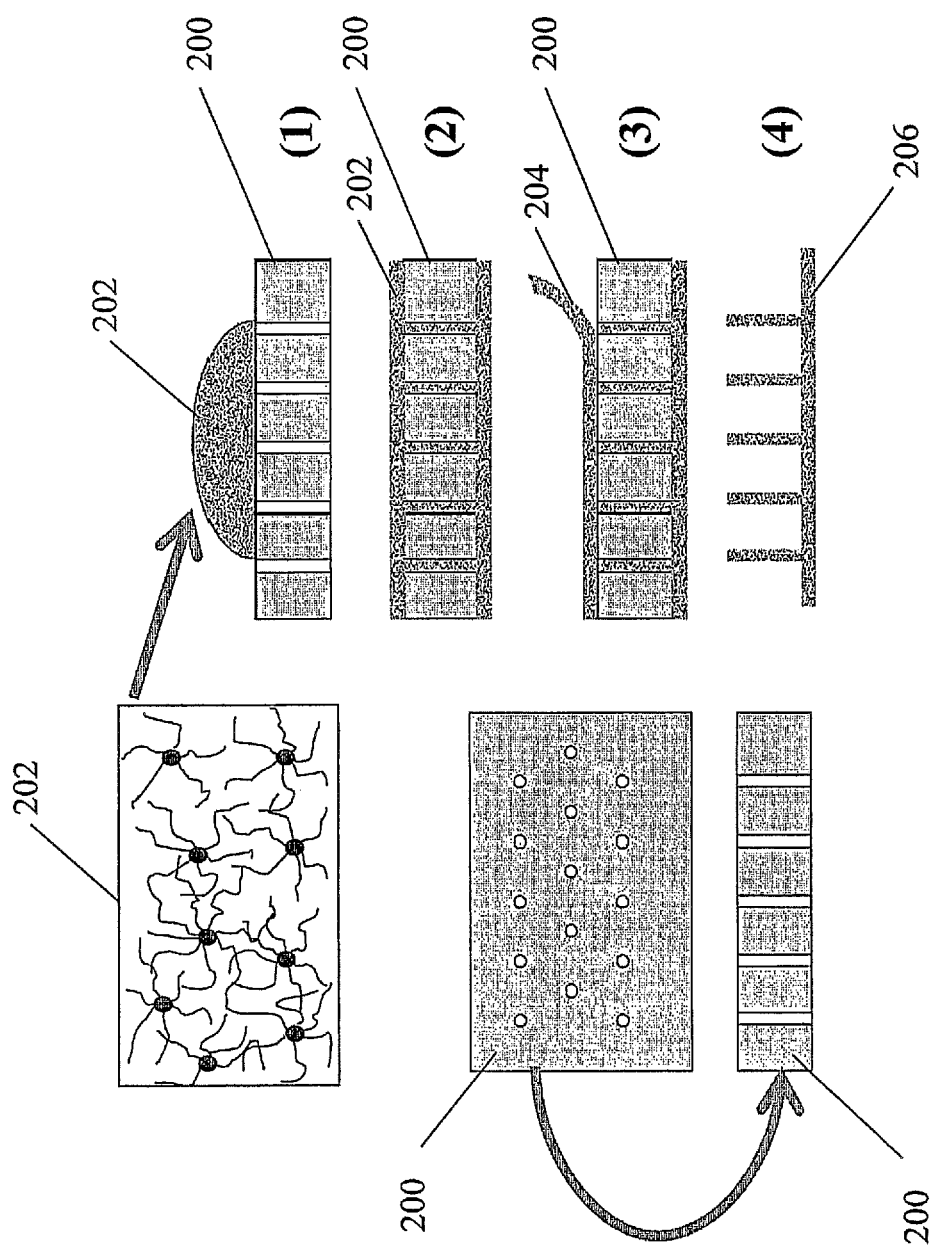
FIG. 2 is a block diagram illustrating an exemplary method of fabricating a micropost array according to an embodiment of the subject matter described herein.

FIG. 2 is a diagram illustrating another exemplary method of fabricating a micropost array according to an embodiment of the subject matter described herein. In addition to a micropost array having some or all microposts including a single piece of ferromagnetic material, a micropost array may also be fabricated wherein the ferromagnetic material is deposited into the uncured micropost material, such as PDMS, prior to array formation. In such an embodiment, the ferromagnetic material may be in the form of particles, rods, dots, beads, etc., such that the microposts will be made up of a composite ferroelastomer. Membrane 200 is a membrane having a plurality of pores. Membrane 200 may serve as a template or mold for micropost array fabrication and may be for example, a track etched membrane. In step 1, membrane 200 is filled with a ferroelastomer material 202, which may be a ferromagnetic-PDMS composite. In step 2, ferroelastomer 202 is cured. If ferroelastomer 202 is cured without further processing, the ferromagnetic particles in the ferroelastomer will have a substantially uniform distribution in each of the resulting microposts. However, in order to increase the ability of a magnetic force to effect movement of each of the microposts, the ferromagnetic particles may be drawn to the top of each of the pores using a magnetic force (not shown) prior to or during the curing process. Each of the resulting microposts will have a higher concentration of ferromagnetic material in the distal end or tip that is not attached to the substrate. As a result, when the microposts are actuated using an applied magnetic field, the resulting movement of each micropost will be greater than that when the ferromagnetic material is uniformly distributed or concentrated towards the substrate end of each micropost. In step 3, the surface layer of cured ferroelastomer 204 is removed, for example, by being peeled off. In step 4, fabricated micropost array 206, having microposts containing a plurality of ferromagnetic particles concentrated at the distal end of each micropost, is removed from membrane 200.

Although these embodiments have been described using a silicon substrate, positive photoresist and photolithography techniques, a negative photoresist or other lithographic techniques and materials may be employed without departing from the intended scope of the presently disclosed subject matter. Further, masks 104 and 110, as well as membrane 200, may be specifically designed and manufactured to be used with a multiwell plate, which is described below.

Figure 3:
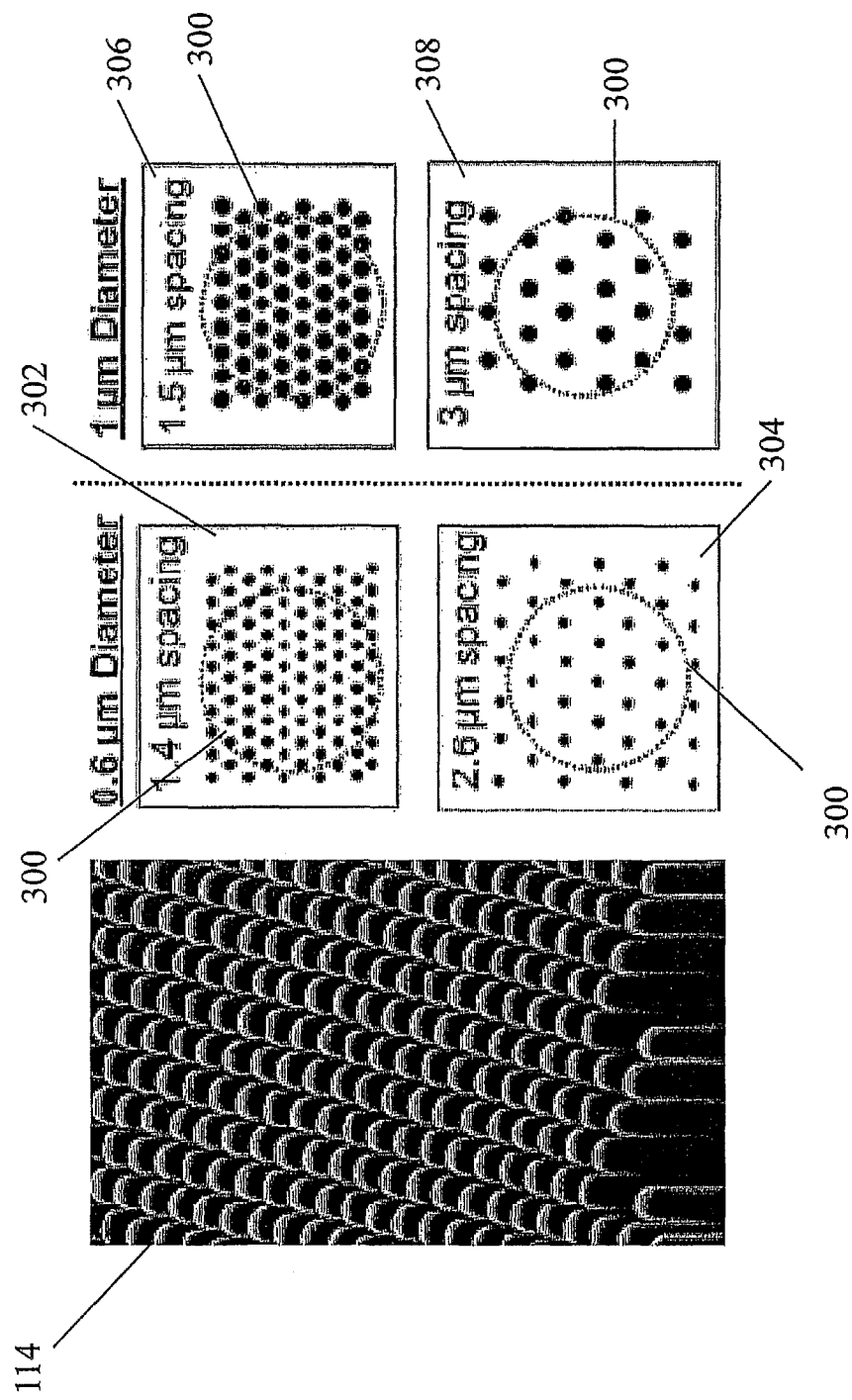
FIG. 3 is a diagram of an exemplary micropost array according to an embodiment of the subject matter described herein.

FIG. 3 is a diagram of an exemplary micropost array according to an embodiment of the subject matter described herein. A scanning electron microscope image of a micropost array 114 is shown. Array 114 may be used with a multiwell microtiter plate, which is explained in detail below. FIG. 3 also depicts possible size and spacing variations for the microposts of micropost array 114 that may be in a well 300 of a multiwell plate. FIG. 3 also depicts that the microposts of an array may vary in size and in proximity with each other on an array. For example, box 302 illustrates microposts that are 0.6 micrometers in diameter and positioned 1.4 micrometers apart from one another. Likewise, box 304 illustrates microposts that are also 0.6 micrometers in diameter, but are spaced 2.6 micrometers apart. Box 306 illustrates microposts of 1 micrometer in diameter that are spaced 1.5 micrometers apart, while box 308 illustrates microposts of 1 micrometer in diameter spaced 3 micrometers apart. It is understood that the size and dimensions depicted in FIG. 3 are for exemplary purposes and do not limit the scope of the present subject matter.

As mentioned above, one technique for measuring the physical or rheological properties of a biofluid specimen is by applying a magnetic force to a micropost that includes magnetic material via magnetic fields. For example, a magnetic micropost of a micropost array such as micropost array 114 may experience a force or torque from magnetic fields and field gradients. Notably, the magnetic force may act on microposts on which a specimen of interest is placed. As indicated above, the specimen may be biofluid, such as blood or mucus. Similarly, the magnetic microposts may be characterized as having one of several magnetic properties (paramagnetic, ferromagnetic, diamagnetic, etc.) and some or all of the microposts in the array may be magnetic. When a magnetic force is applied to the microposts, the microposts containing ferromagnetic material move in a way that is characteristic of the applied magnetic force and the forces that are imposed by the biofluid specimen. The motion of a micropost as influenced by the magnetic field may then be measured. The response of the micropost to the magnetic field can also be used as a measure of the specimen's mechanical properties, such as inherent linear and non-linear viscoelastic properties, and physical properties.

Figure 4:
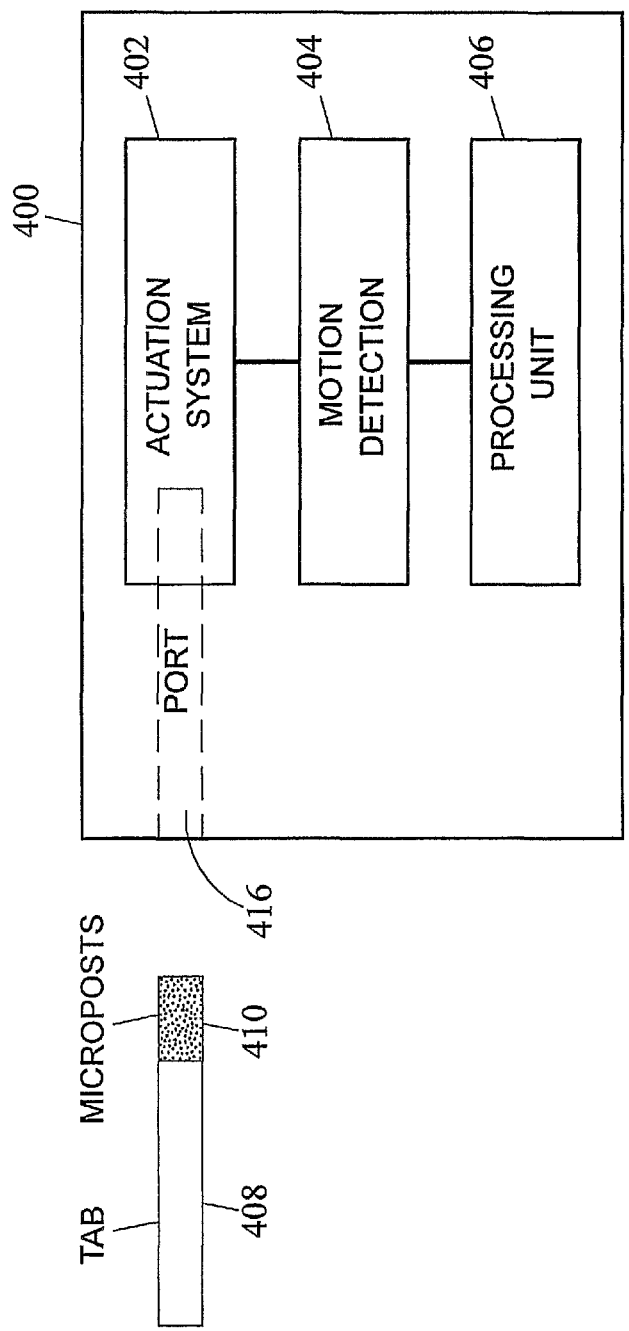
FIG. 4 is a block diagram illustrating an exemplary point of care system according to an embodiment of the subject matter described herein.

In one embodiment, the present subject matter includes a standalone device that is adapted to test various properties of a biofluid specimen. One such embodiment of a standalone device for testing properties of a biofluid specimen includes a point of care (POC) handheld device. For example, FIG. 4 is a block diagram illustrating an exemplary point of care system according to an embodiment of the subject matter described herein. In one embodiment, the present subject matter may be implemented as a point of care system embodied within a portable device. FIG. 4 depicts a portable device 400 that includes an actuation system 402, a motion detection system 404, and a processing unit 406. Device 400 may also include an ingress port 416, which is adapted to receive an inserted disposable tab 408. Tab 408 may include an end portion 410, which comprises a micropost array such as micropost array 114. The end portion 410 is configured to receive a small sample size of a biofluid specimen (e.g., blood, mucus, synovial fluid, etc.). The microposts, or cilia, as described above, may include silicone-based pillars or microposts, some of which may contain a ferromagnetic material at the distal end (i.e., the end that is not attached to the substrate base). In one embodiment, the microposts may be vertically-aligned. The microposts may also be stamped with a substance such as fibronectin, an extracellular matrix protein, to attract cells when placed on micropost tips. In one embodiment, tab 408 may be inserted in port 416 such that end portion 410 containing the specimen is close enough to actuation system 402 for a actuation force (e.g., a magnetic force) generated by actuation system 402 to effect movement of the microposts.

In one embodiment, actuation system 402 includes a low-power system (i.e., which may be electrically powered by either a small battery or manual actuation produced by a small hand-crank). For example, actuation system 402 may include a small spinning permanent magnet adapted to generate a time varying magnetic field. Device 400 may be controlled by a user to apply the magnetic field to end portion 410 of tab 408, thereby causing motion (e.g., oscillation) of microposts on the end portion 410. As the microposts are compelled to move by actuation system 402, motion detection system 404 may measure and record the movement of the microposts on end portion 410. In one embodiment, motion detection system 404 may comprise a magnetic pickup coil that produces current based on the movement of the microposts in a magnetic field. For example, motion detection system 404 may then be used to measure the amplitude and/or the phase of the generated current in the magnetic pickup coil. The amplitude and phase of the generated current corresponds to the motion of the microposts. In an alternate embodiment, motion detection system 404 may instead include an imaging system that detects movement of the microposts using a camera or other suitable imaging apparatus. In other implementations, motion detection system 404 may measure the scattering, transmission, or reflection of light by the microposts. In such an implementation, the tips of the microposts that are not attached to the substrate may be metalized or otherwise treated with a reflective material to make the microposts scatter light.

The data produced by motion detection system 404 may be forwarded to processing unit 406 for calculations and analysis. Alternatively, device 400 may be provisioned with a radio uplink (not shown) to wirelessly provide the data to a processing unit on a separate computer. The calculations and analysis performed by the processing unit may include determining a measure of fluid rheology based on the force applied by actuation system 402 and the resulting motion detected by motion detection system 404.

Figure 5:
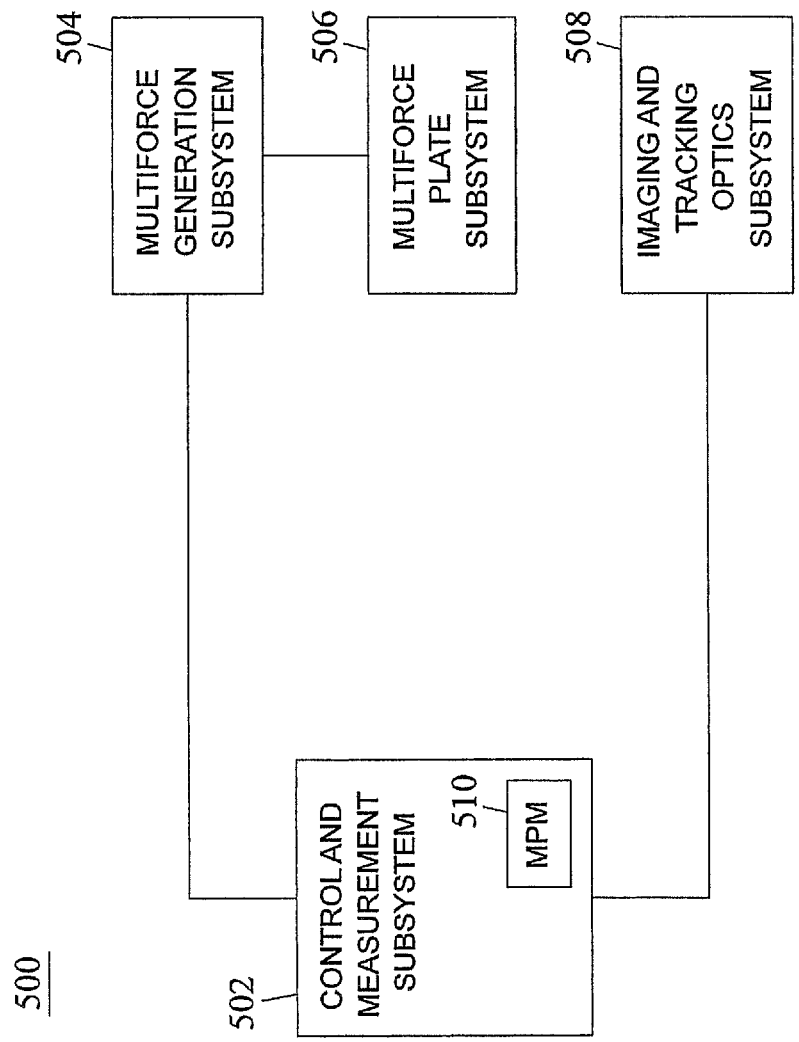
FIG. 5 is a block diagram illustrating an exemplary high-throughput screening system according to an embodiment of the subject matter described herein.

FIG. 5 is a block diagram illustrating an exemplary high-throughput screening system according to an embodiment of the subject matter described herein. In one implementation, the actuation and optical system may be similar to that described in International Patent Application Publication No. WO 2008/103430, the disclosure of which is incorporated herein by reference. High-throughput screening system 500 is capable of applying a force and measuring micropost responses. Generally speaking, system 500 includes a control and measurement subsystem 502, a multiforce generation subsystem 504, a multiforce plate subsystem 506, and an imaging and tracking optical subsystem 508.

The actuation and motion detection systems for a high-throughput screening system, i.e. multiforce generation subsystem 504 and imaging and tracking optics subsystem 508, may be similar in operation to those described above for the point of care system. One physical difference between an actuation system for a high-throughput screening system and a point of care system is that the actuation system may be replicated for each well or small group of adjacent wells in a multiwell microtiter plate. The motion detection system for a multiwell microtiter plate may include, but is not limited to, an optical system that measures scattered light to detect movement of the microposts, an imaging system including a camera that images each well or group of wells in the microtiter plate, or a pick up coil that measures amplitude and phase of a current produced by motion the microposts in each well.

Figure 7A:
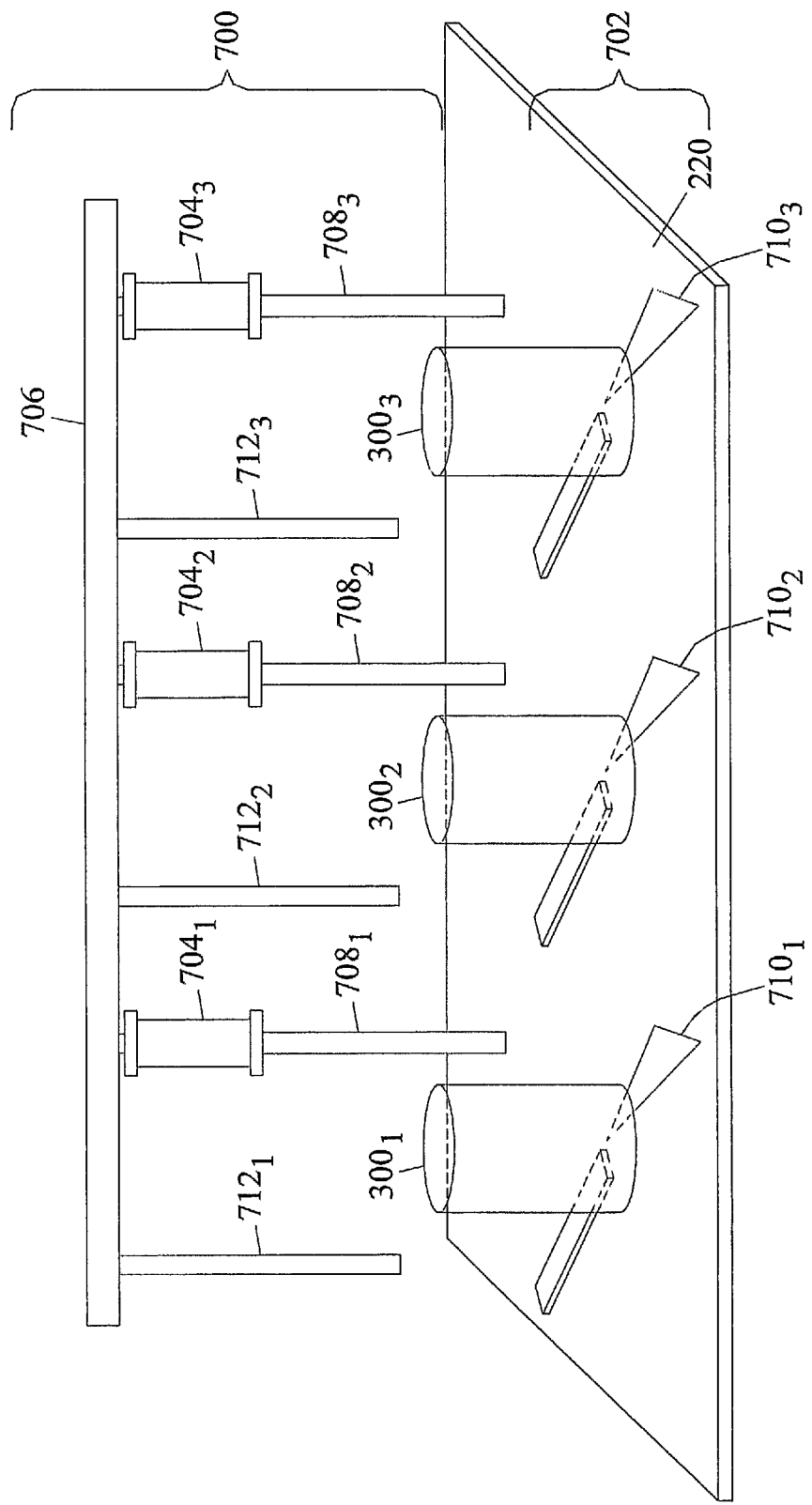
FIG. 7A is a diagram depicting exemplary separation of the exciter assembly from the multiforce plate of a multiforce high-throughput system according to an embodiment of the subject matter described herein.

In one embodiment, multiforce generation subsystem 504 comprises a magnetic drive block, such as exciter assembly 700, which is shown in FIG. 7A. Subsystem 504 may also include an appropriate cooling mechanism (not shown) to dissipate excess heat or to maintain system 500 at a target temperature. In one embodiment, subsystem 504 is capable of producing forces of significant magnitude (e.g., forces greater than 10 nanoNewtons), in multiple directions over a three dimensional sphere, and can be varied at frequencies up to more than three kilohertz.

High-throughput screening system 500 also includes a multiforce plate subsystem 506. Multiforce plate subsystem 506 may comprise a microtiter well plate, such as multiwell plate 600, shown in FIG. 6, which includes a plurality of specimen wells 300. The well plate may also be coupled with a cover glass sheet that serves as the bottom of the well plate. Multiforce plate subsystem 506 may also include a plurality of field-forming poles that are used to form a magnetic (or electric) coupling with excitation poles of multiforce generation subsystem 504. This is better illustrated in FIG. 7A where multiforce plate subsystem 506 is represented as multiforce plate 702.

Control and measurement subsystem 502 may also include a mechanical properties module 510 that is used to measure the mechanical properties of the specimen depending on the measured movement of the microposts. An imaging and tracking optical system 508 may also be employed to perform several kinds of measurements, either simultaneously with the application of force or after the force sequence has been applied. For example, optical system 508 may include a single specimen imaging system with a robotic stage that can systematically position each well 300 over a microscope objective. Alternatively, optical system 508 may include an array based system that is capable of imaging several wells simultaneously. The recorded images may be used to track the micropost position and the like.

Figure 6:
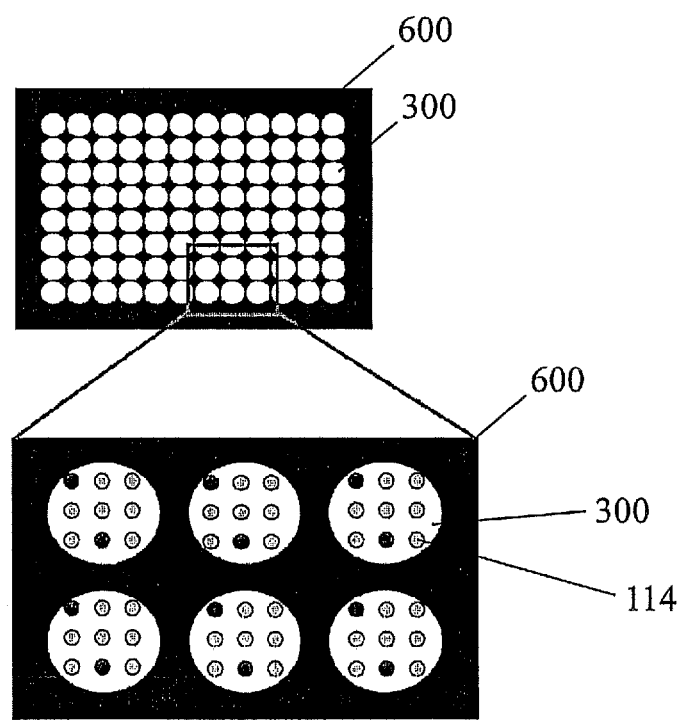
FIG. 6 is a diagram of an exemplary multiwell plate according to an embodiment of the subject matter described herein.

FIG. 6 illustrates an exemplary multiwell plate according to an embodiment of the subject matter described herein. Multiwell plate 600 includes a plurality of specimen wells 300. Each specimen well includes microposts from at least a portion of micropost array 114. In one embodiment, multiwell plate 600 is a bottomless multiwell microtiter plate. In such an embodiment, one side of multiwell plate 600 may be "inked" with uncured micropost material, e.g. PDMS, and pressed onto micropost array 114, then cured, such that the PDMS "ink" acts as glue and adheres multiwell plate 600 to micropost array 114. FIG. 6 illustrates such an embodiment, as viewed from above. Although system 500 was initially designed to be utilized with a standard 96 well plate geometry (e.g., a conventional microtiter plate, as shown), system 500 may easily be adapted to accommodate a smaller or larger number of wells.

FIG. 7A is a diagram depicting exemplary separation of the exciter assembly from the multiforce plate of a multiforce high-throughput system according to an embodiment of the subject matter described herein. Referring to FIG. 7A, exciter assembly 700 may include a plurality of excitation poles 708, each of which may include a coil 704. Coils 704, which generate the magnetic field, may include standard wire-wrapped bobbins or, alternatively, the coils may be patterned on a multilayer printed circuit board. The latter embodiment is especially well suited for tight spatial constraints that may be imposed by high numerical aperture microscopy or smaller well layouts. Excitation poles 708 may be attached to a magnetic flux return plate 706. In one embodiment, excitation poles 708 and flux return plate 706 may be made from a high permeability material, such as soft iron. Multiforce plate 702 includes a plurality of specimen wells 300 that are adjacent to field-forming poles 710. Specimen wells 300 may include specimen chambers of a microtiter well plate. In one embodiment, field-forming poles 710 may be fabricated from thin sheets of magnetic material (e.g., laser cutting from sheet magnetic material or by electrodeposition using a photolithography mask) and are responsible for carrying the flux delivered by excitation poles 708 to the microposts in specimen well 300.

Notably, field-forming poles 710 may be positioned in proximity to wells 300. Each well 300 may contain at least a portion of micropost array 114. In one embodiment, microposts of micropost array 114 may include microposts containing ferromagnetic material that may be magnetized or ferroelectric material that may be polarized. In a magnetic application, magnetic microposts can include paramagnetic or diamagnetic material. In an electrical application, microposts of micropost array 114 can contain polarized, charged or chargeable particles. FIG. 7A shows that the force is not activated since excitation poles 708 have not been brought into proximity or contact with field-forming poles 710 of multiforce plate 702, (and coils 704 have not been energized). Notably, in an embodiment where the actuation is caused by magnetic force, excitation poles 708 and field-forming poles 710 do not need to physically touch; once the excitation pole is brought into proximity of the field-forming pole, and the coil is activated, the magnetic circuit is complete, a magnetic field is generated and the magnetic microposts of micropost array 714 are actuated.

FIG. 7B is a diagram illustrating a cross-section view of a multiforce high-throughput screening system according to an embodiment of the subject matter described herein. FIG. 7B depicts the different sections of a pole plate comprising a bonded field-forming pole/cover glass sheet combination. Cover glass plate 714 (which includes bonded field-forming poles 710) is further bonded to a bottomless well plate 600 and micropost array 114 to create an assembled multiforce plate, 702. Each specimen well 300 will contain at least a portion of microposts from micropost array 114. Exciter assembly 700 is shown above plate 702. In one embodiment, optical system 508 may include the placement of a lens in an illumination aperture 716 of exciter assembly 700.

In one embodiment, the typical operation of system 500 involves the multiforce plate 702 being loaded with specimens, processed, and then engaged with exciter assembly 700. Together, the combined system may be placed above an inverted microscope objective to measure micropost motion during the application of force via a magnetic field. Alternatively, micropost motion may be measured or observed through change in current in a pick-up coil, as described above.

In one embodiment, control and measurement subsystem 502 may be designed to be computer controlled and is able to generate flux from each of coils 704. The control of the magnetic flux at each coil 704 is achieved by coordinating the currents in the coils so that the coils generate flux either in a limited set of nearby specimen wells 300, or generate fields and forces in every well on multiforce plate 704. Equations to determine which coils to activate for a given configuration of activated specimen wells may be solved by standard linear equations of circuit theory, with known correspondences between magnetic circuit and electrical circuit quantities.

Figure 8A:
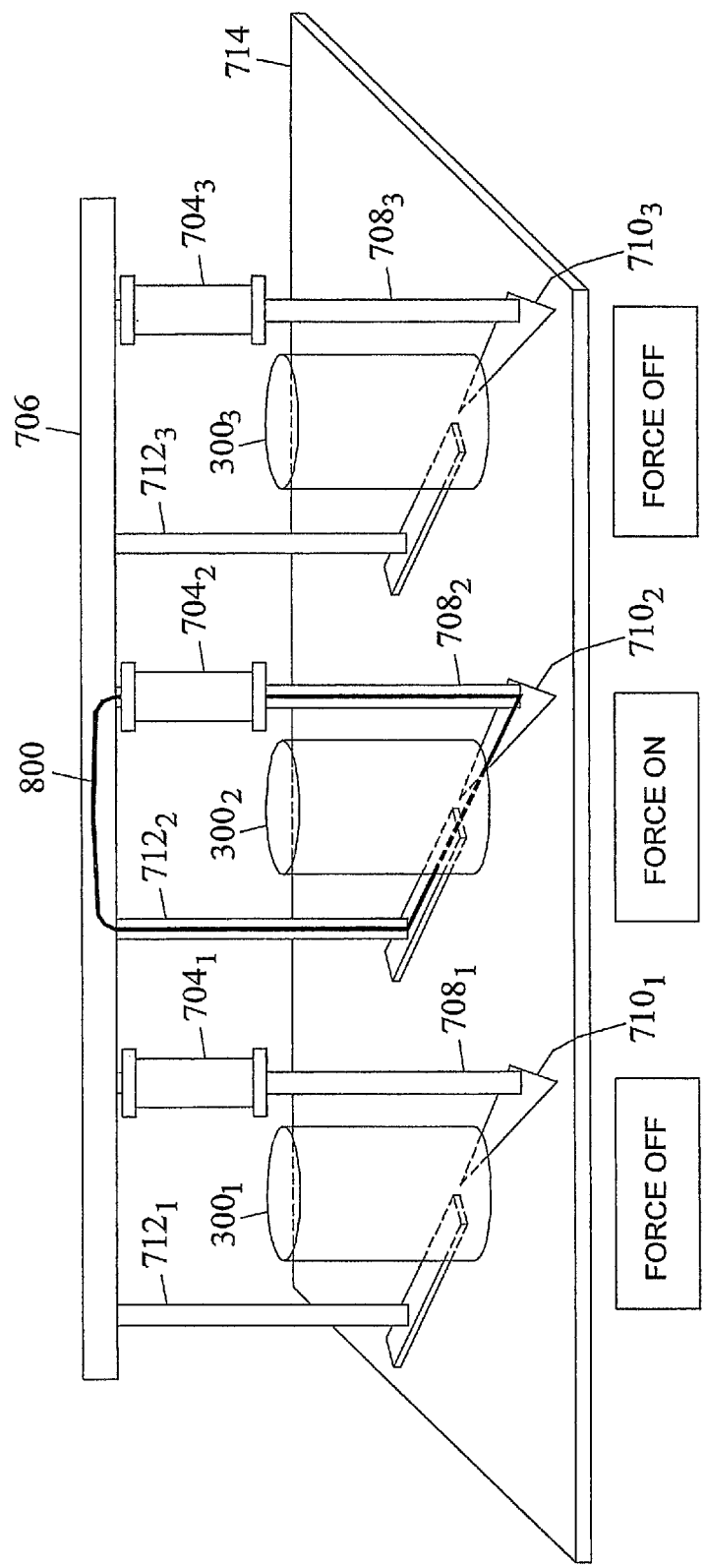
FIG. 8A is a diagram illustrating selectively exciting a single well of a multiforce plate according to an embodiment of the subject matter described herein.

In addition to applying a magnetic field to a plurality of specimen wells, the present subject matter is also capable of selectively powering a single designated well in a multiforce plate according to one embodiment of the subject matter described herein. FIG. 8A is a diagram illustrating selectively exciting a single well of a multiforce plate according to an embodiment of the subject matter described herein. In FIG. 8A, flux return plate 706 represents a sheet of high permeability magnetic material that serves as a path for the return of magnetic flux. The cylinders represent coils 704 that are responsible for generating the flux to be delivered via excitation poles 708. Cover glass plate 714 represents the bottom of a multiwell plate (e.g., a microtiter plate) which is depicted as a plurality of specimen wells 300, each of which include at least a portion of micropost array 114. In one embodiment, cover glass plate 714 is integrated with thin foil field-forming poles 710 to form a pole plate. The magnetic drive block or exciter assembly 700 has a single magnetic flux return plate 706 that is coupled to excitation poles 708 that may be positioned to contact this layer of field-forming poles 710. In addition to excitation poles 708 that generate flux (via coils 704), exciter assembly 700 may include flux return posts 712 which are not equipped with coils. Flux return posts 712 are adapted to complete the magnetic circuit by providing a return path to flux return plate 706. By providing a return path for the flux for each separate well, control over individual wells may be achieved. For example, the fields and forces applied to a given specimen well are primarily generated by the current in the coil feeding that particular specimen well. This is shown in FIG. 8A where excitation poles 708 and flux return posts 712 are brought into contact with field-forming poles 710. Specifically, because excitation pole $708_2$ is brought into contact with field-forming pole $710_2$ and coil $704_2$ is activated, only magnetic flux 800 is generated. Flux 800 is shown as a line that circles through the current coil $704_2$, to field-forming pole $710_2$, across the gap in specimen well $300_2$, back up through flux return post $712_2$, and then through magnetic flux return plate 706 to complete the magnetic circuit. Notably, flux is not present in specimen wells $300_1$ and $300_3$ because coils $704_1$ and $704_3$ are not activated.

In an alternative embodiment, magnetic flux return plate 706 may be replaced by a local return path that serves each coil 704. This may include a cylindrical cap over each coil 704, with flux routed from one end of coil 704 through field-forming pole 710 and back through the outer cylinder to the other end of the coil 704. This implementation may be useful for isolating each well 300 from all of the other wells and by allowing maximum flexibility in the experimental methodology.

Figure 8B:
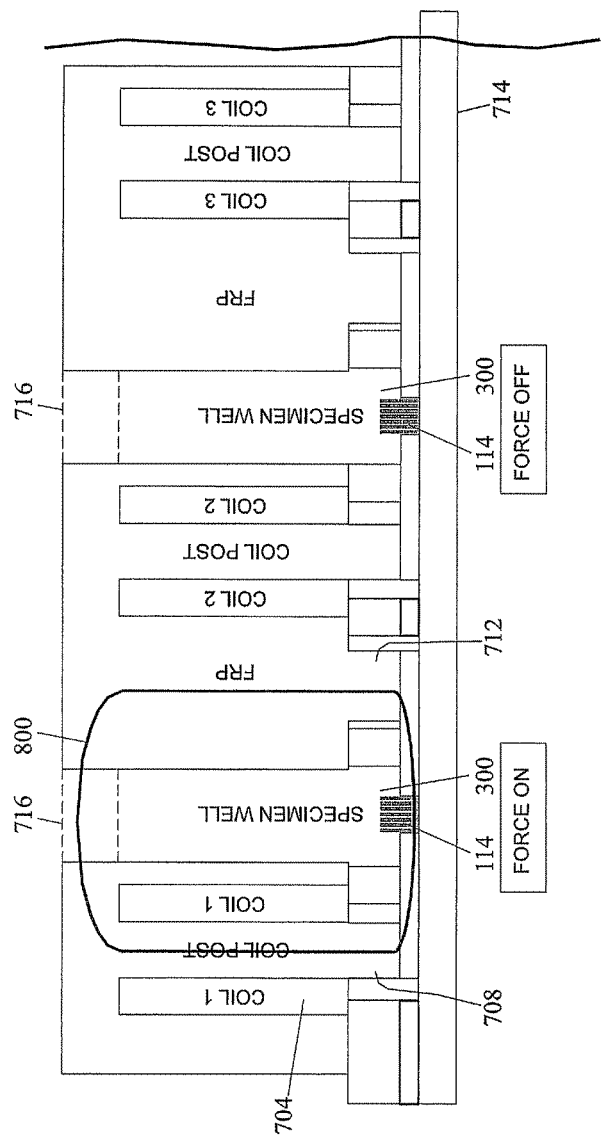
FIG. 8B is a diagram illustrating operation of a multiforce high-throughput screening system according to an embodiment of the subject matter described herein.

FIG. 8B illustrates the coupling of exciter assembly 700 and assembled multiforce plate 702. Notably, FIG. 8B illustrates exciter assembly 700 being brought into magnetic contact with field-forming poles 710 which are integrated with specimen wells 300 of multiforce plate 702. In order to generate the magnetic force, excitation poles 708 need to be coupled to field-forming poles 710 and coils 704 need to be energized. More specifically, magnetic flux is generated by the set of coils 704 that is magnetically coupled to a flux return path to minimize the magnetic circuit reluctance. For example, excitation poles 708 carry the flux from coils 704 to field-forming poles 710 and then back to magnetic flux return plate 706 (via flux return posts that are described above). In this way, a magnetic circuit is created that affords relatively low circuit reluctance and generates significant magnetic fields and forces at field-forming poles 710. In this configuration, each field-forming pole 710 in the multiforce plate 702 is driven by an excitation pole 708.

The path of the flux 800 is shown as a solid line that closes on itself linking a coil 704 in exciter assembly 700. In this configuration, each coil is assigned to one specimen well. When the coil 704 receives current, flux 800 is generated in excitation pole 708 and coupled to a corresponding field-forming pole, thereby applying a force to a magnetic material, such as a magnetic micropost of micropost array 114, in the corresponding specimen well 300. Notably, the flux path of flux 800 is localized to a single specimen well.

In one embodiment, the present subject matter may be used to apply an electric field to electrically charged particles or molecules in at least some microposts of specimen well 300. This may be accomplished by applying an electrical potential to the excitation pole (instead of applying a magnetic potential via the coil winding) and coupling it to the field-forming pole to form an electric field in the specimen well which in turn causes microposts having polarized or charged particles to move.

It should be noted that FIGS. 7B and 8B show the operation of the designed system where a schematic cross section of exciter assembly 700 is located over multiforce plate 702. It should be noted that FIGS. 7B and 8B are illustrated in schematic form whose geometry is representative of the relationship between coils, specimen wells, and flux return path. The actual design may not have a "cut" cross section as depicted in FIGS. 7B and 8B. In an alternate embodiment, exciter assembly 700 may be located below multiforce plate 702, with excitation poles 708 pointing upwards. Additionally, in other embodiments, multiwell plate 600 may first be attached to micropost array 114, with the combination then being placed on top of a pole plate.

Figure 9A:
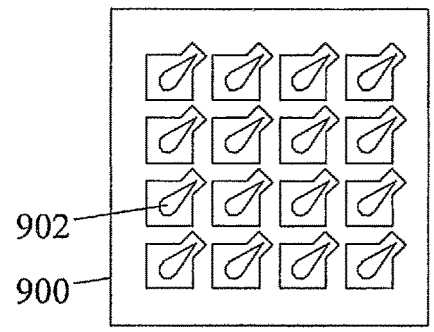
FIGS. 9A and 9B are diagrams of exemplary arrays of field-forming poles suitable for use with embodiments of the subject matter described herein.
Figure 9B:
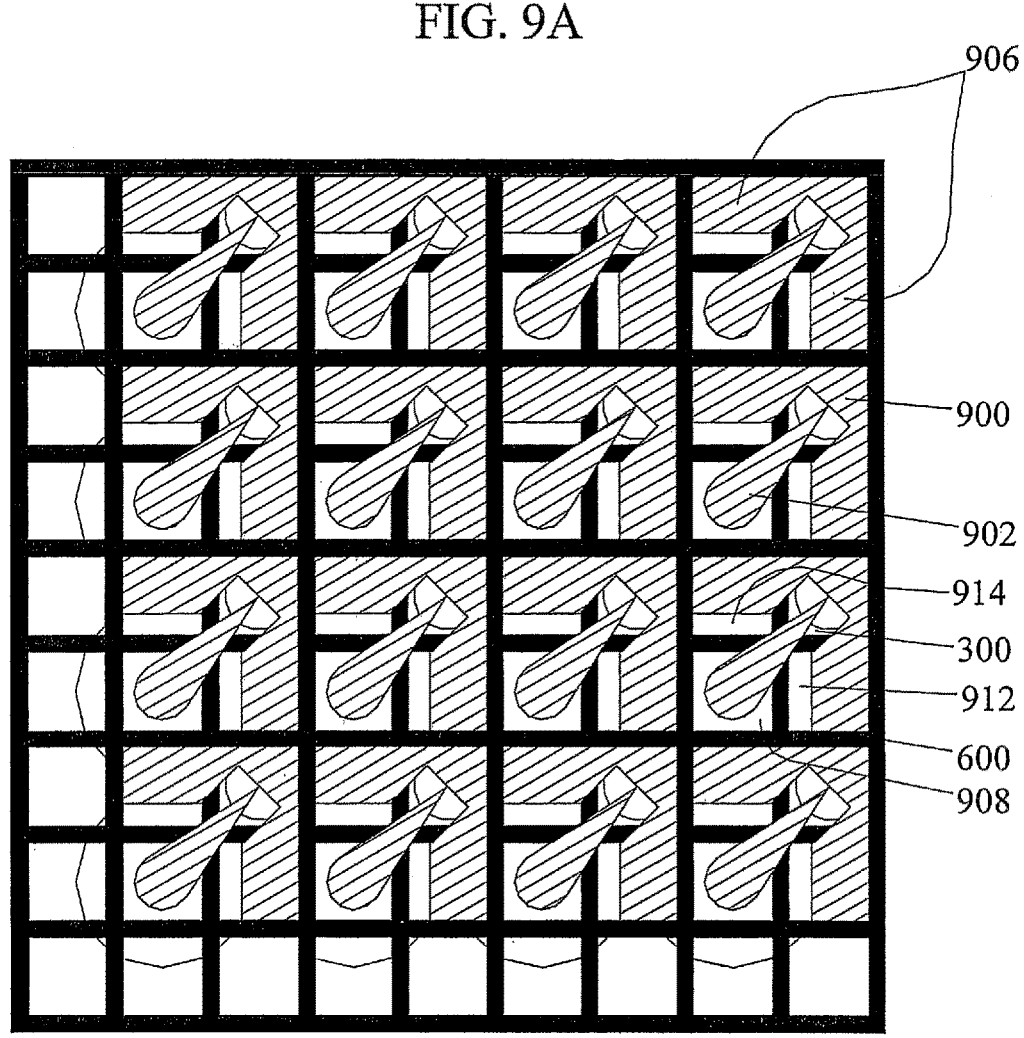
Figure 10:
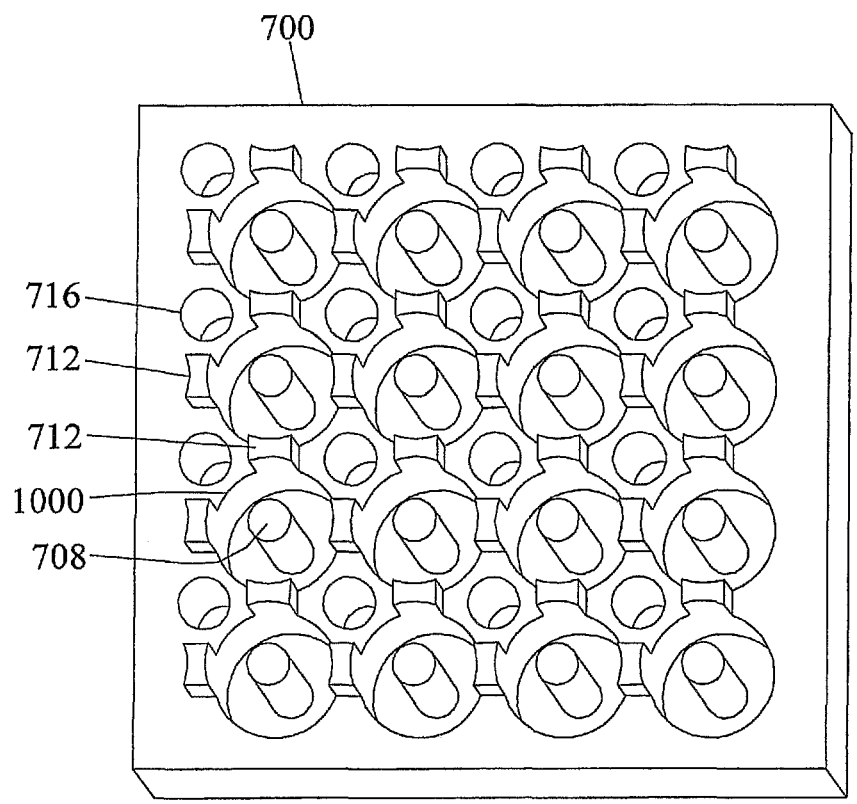
FIG. 10 is a diagram of a magnetic core of an exciter assembly suitable for use with embodiments of the subject matter described herein.

FIGS. 9A and 9B are diagrams of arrays of exemplary field-forming poles suitable for use with embodiments of the subject matter described herein. In one embodiment, "pole pattern laminates" are designed to form the bottom of the multiforce plate. FIGS. 9A and 9B show an exemplary 4×4 array of field-forming poles 710 that may have been etched in a foil sheet (e.g., permalloy) using a combination of lithography and wet chemical etching. The field-forming poles may be bonded to a cover glass sheet (i.e., to make a pole plate) that is suitable for high resolution microscopy. This bonded sheet may then be affixed to the underside of a bottomless multiwell plate, such as a conventional microtiter plate. FIG. 9A illustrates a particular design of a pole plate 900. In one embodiment, pole plate 900 may include a sheet of magnetic permalloy foil etched to create "pole-flat" regions in which a sharp pole tip is located near a flat one to form a high gradient magnetic field. FIG. 9B shows that the rounded end of a "tear drop" piece 902 fills one of the wells. The flux from the "tip" of piece 902 re-enters the metal film in the opposite flat whose "wings" 906 cover the other two neighboring wells. A coil post 708, i.e., an excitation pole, is aligned to couple to the rounded end of the teardrop shaped piece 902, while two flux return posts 712 in the other two neighboring wells are aligned to couple to wings 906. The high gradient field location where the sharp tip opposes the flat one is arranged to be in the specimen well. When exciter assembly 704 is placed on top of the multiforce plate, illumination apertures 716 (as shown in FIG. 10) of exciter assembly 714 align with the specimen wells.

FIG. 9B also illustrates that when pole plate 900 is bonded to the bottom of a multiwell plate to form a multiforce plate, it leaves every fourth well for specimens, with the rest of the wells used to accommodate excitation poles 708 and flux return posts 712. Notably, FIG. 9B depicts how the present subject matter appears from the viewpoint of pole plate 900 overlaid on top of a multiwell plate 600, which in turn is coupled to an exciter or coil assembly on the opposing side. As shown in FIG. 9B, the multiwell plate and pole plate combination may be "conceptually" divided in 2×2 well sections. Specifically, for each specimen well (e.g., well 300), one well (e.g., well 908) is used to carry flux from an excitation pole 708, while the two neighboring wells (e.g., wells 912 and 914) are used to return flux to the magnetic flux return plate. The fact that the return paths from the wells are connected together does not matter within the scope of magnetic circuits, as this is comparable to having a ground plane in an electrical circuit.

Multiforce plate 702 may be designed to have field-forming poles 710 to be in contact with or proximity to all of the wells 300 simultaneously. In one embodiment, field-forming poles 710 may be separate from exciter assembly 700 for convenient changing of the field configuration at the specimen array. In addition, multiforce plate 702 may be either incorporated into the specimen array (i.e., multiwell plate) or be separate. In one embodiment, multiforce plate 702 is incorporated into the multiwell plate so that each well 300 has a number of field-forming poles 710 projecting into the specimen well to interact with the microposts of micropost array 114 located in specimen well 300.

Many other field-forming pole configurations may be envisioned in the specimen well. One possible configuration may include a "pole-pole" geometry which entails two identical poles that may have large forces near each of them, but due to symmetry, have low force in the center. Similarly, a "comb" geometry with multiple sharp tips, each providing force near its region, has been considered. The "comb" configuration may provide larger effective "force-area" product allowing for the application of significant force to more microposts within the specimen well.

FIG. 10 illustrates an exemplary exciter assembly 700 that may be used by the present subject matter. Exciter assembly 700 includes coil posts 708, flux return posts 712, and illumination apertures 716. Although FIG. 10 only depicts a 4×4 array embodiment, a full scale exciter assembly may be manufactured to cover a conventional 384 well multiwell plate. The exciter assembly would then include 96 illumination apertures, which are open holes to allow for transmission microscopy. More specifically, an exciter assembly designed for a 384 multiwell plate uses three out of four wells for the magnetic system, leaving 96 wells active for specimens. That is, for every 4 holes (2×2 array) of the multiwell plate, two are used for flux return posts 712, one is used for illumination aperture 716, and one is used for coil post 708.

The cylindrical openings 1000 containing the central coil posts 708 are used to hold the coils that generate flux (e.g., a wire may be wrapped around coil post 708 and contained within cylindrical opening 1000). The flux passes through the central post 708 and is coupled into the field-forming poles that are mounted to the pole plate on the bottom of a multiforce plate. The flux returns through flux return posts 712 that enter through the multiforce plate through two wells neighboring the specimen well. In one embodiment, exciter assembly 700 may be machined from soft iron for high permeability and saturation, and low hysteresis.

Figure 11:
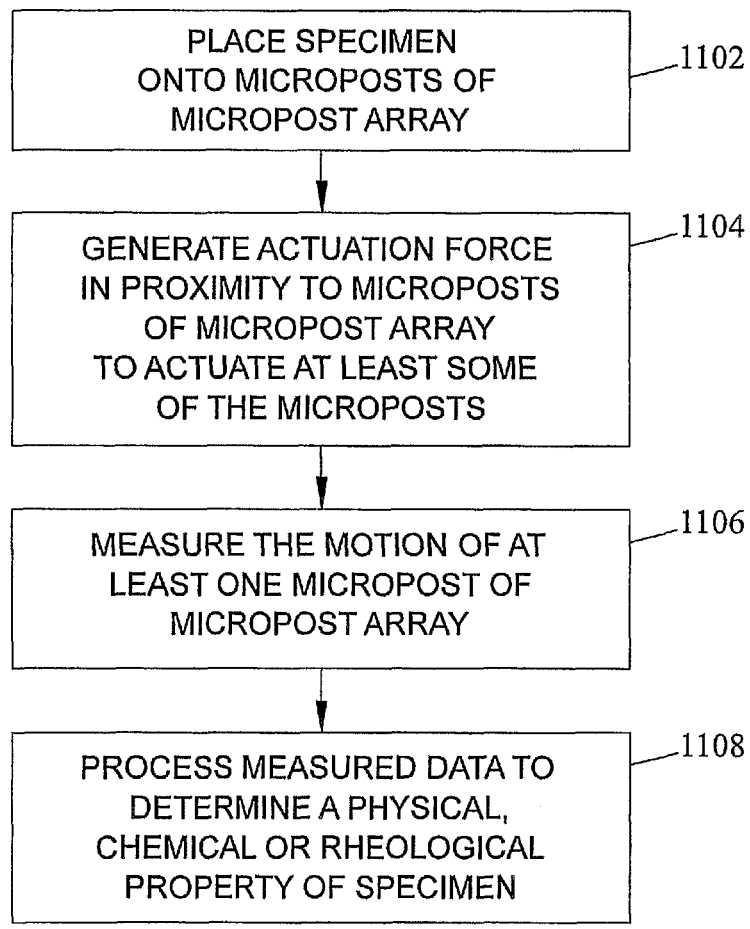
FIG. 11 is a flow chart illustrating an exemplary process for determining physical, chemical, or rheological property of a specimen according to an embodiment of the subject matter described herein.

FIG. 11 is a flow chart illustrating an exemplary process 1100 for determining physical, chemical, or rheological property of a specimen according to an embodiment of the subject matter described herein. Referring to FIG. 11, in block 1102, a specimen is placed on microposts of a micropost array, such as, for example, the microposts in wells 300 of a multiforce plate, each well containing at least a portion of micropost array 114. In block 1104, an actuation force is generated in proximity to the microposts. Continuing with this example, the multiforce plate is provided with field-forming poles at positions corresponding to the specimen wells, wherein the field-forming poles may be used to form fields. In one embodiment, the field-forming poles are used to form at least one of an electric or magnetic field in the vicinity of the field-forming poles. The field-forming poles apply force via the electric or magnetic field and/or their gradients to the microposts located in the wells in order to move the microposts and test the physical or rheological properties of the specimens in the wells.

In block 1106, the effect on the microposts, such as those within specimen well 300, is measured. In one embodiment, the exhibited motion of all the microposts is measured, and may be averaged for use in determining a property of the specimen. In another embodiment, the movement of one or more particular microposts or groups of microposts may be measured and used in calculations.

In block 1108, the measured data is processed to determine at least one of a physical, chemical or rheological property of the specimen.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of fabricating a micropost array having a plurality of microposts extending outwards from a substrate, comprising:

filling pores in a substrate with a curable material, such that the curable material interconnects the plurality of pores along at least one planar surface of the substrate, wherein the curable material is flexible when cured and includes a plurality of nanoparticles;

applying a force to draw the plurality of nanoparticles in one direction such that the concentration of nanoparticles is non-uniform within the pores;

curing the curable material; and removing the substrate to form the micropost array.

2. The method of claim 1 wherein the plurality of nanoparticles has at least one of a metallic, magnetic, reflective, and ferroelectric characteristic.

3. The method of claim 1 wherein, after removing the substrate, the microposts are coated obliquely with a material.

4. The method of claim 1 wherein the plurality of pores are vertically-aligned.

* * * * *